US006485718B1

(12) United States Patent
Parthasarathy et al.

(10) Patent No.: US 6,485,718 B1
(45) Date of Patent: Nov. 26, 2002

(54) SITE SPECIFIC LIGATION OF PROTEINS TO SYNTHETIC PARTICLES

(75) Inventors: Rajani V. Parthasarathy, Woodbury, MN (US); Stephen C. Lee, Creve Coeur, MO (US)

(73) Assignee: Pharmacia Corporation, St. Louis, MO (US)

( * ) Notice: Subject to any disclaimer, the term of this patent is extended or adjusted under 35 U.S.C. 154(b) by 0 days.

(21) Appl. No.: 09/547,008

(22) Filed: Apr. 11, 2000

Related U.S. Application Data
(60) Provisional application No. 60/129,105, filed on Apr. 13, 1999.

(51) Int. Cl.[7] .................. A61K 31/74; A61K 47/48; A61K 38/00; C07K 1/00
(52) U.S. Cl. ............ 424/78.17; 530/300; 530/350
(58) Field of Search .................. 530/300, 350; 424/78.17

(56) References Cited

U.S. PATENT DOCUMENTS 5,527,524 A * 6/1996 Tomalia et al. ............ 424/1.33

FOREIGN PATENT DOCUMENTS

WO        WO 96/11953      * 4/1996

* cited by examiner

Primary Examiner—Jezia Riley
(74) Attorney, Agent, or Firm—Alan L. Scrivner; Rachel A. Polster

(57) ABSTRACT

The present invention relates to site-specific conjugation of synthetic particles to proteins.

1 Claim, 3 Drawing Sheets

Figure 1:
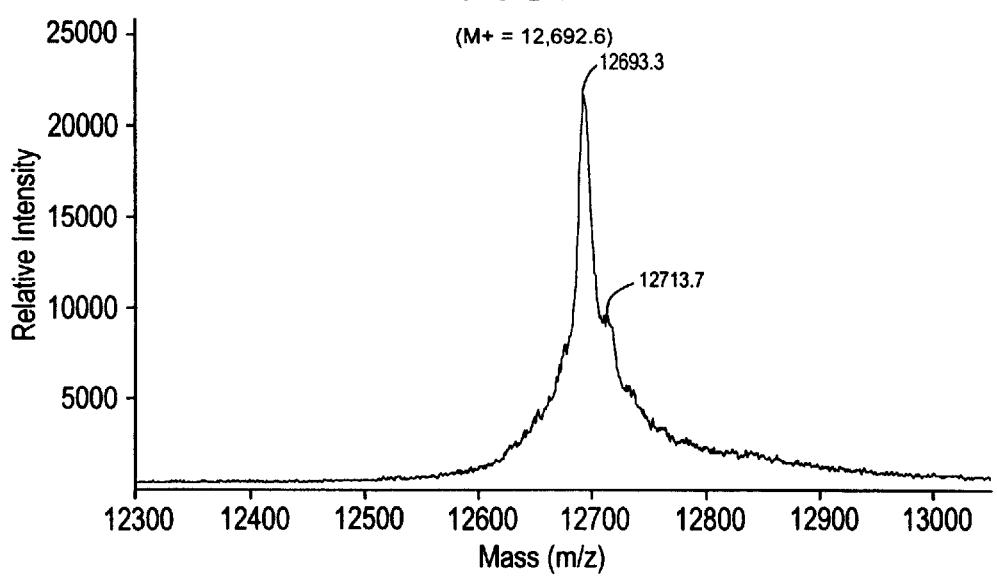

Linear MALDI Mass Spec of
Tryptic Digest of Activated Cytokine

SITE SPECIFIC LIGATION OF PROTEINS TO SYNTHETIC PARTICLES

This application claims priority to U.S. Provisional Patent Application Ser. No. 60/129,105 filed Apr. 13, 1999.

FIELD OF INVENTION

The present invention relates to the field of site-specific conjugation of synthetic particles to proteins. Synthetic particles include monodisperse synthetic particles, highly monodisperse nanoscale particles, and dendritic polymers (herein after dendrimers). Proteins include four-helical bundle proteins and cytokines. The present invention also relates to both novel methods of conjugation of synthetic particles to proteins and the resulting compositions.

BACKGROUND OF THE INVENTION

Biotechnology has made the production and engineering of proteins a straight-forward commercially feasible technology. Recombinant proteins are linear amino acid polymers, synthesized from amino to carboxy ends, that fold into three dimensional configurations during or after synthesis. Biotechnology allows convenient production of individual protein molecules in bulk. Bioconjugate technology can add an additional dimension to protein structures by allowing higher-order organization of the individual proteins using a synthetic framework. Advantages of higher order structures containing proteins include, under some circumstances, therapeutically important properties including, but not limited to, circulating half-life, tissue or intracellular targeting, biodistribution, protein stability, ligand potency/activity, and protein immunogenicity. Regulating the relative positions and stoichiometries of individual proteins in higher order structures can also give rise to wholly new activities and functions.

PEG (polyethylene glycol)is a synthetic material commonly attached to proteins. A variety of means have been used to attach PEG to proteins. The most frequent method of attachment is through the amino groups as found on the lysine residues or at the N-terminus (See PCT Application WO 96/11953, incorporated by reference).

Kinstler et al., WO 96/11953 teaches that conjugation of PEG to a particular protein, namely G-CSF, by conventional means has deficiencies related to the poor site-specificity of the PEG conjugation. Kinstler identified that although the prior art provided multiple methods of conjugating PEG to proteins, none of the methods known in the art allowed for selective attachment. As noted above, selective attachment is desirable for many reasons including retention of protein bioactivity. Kinstler identified a method of bioconjugation to selectively attach PEG to the N-terminus of G-CSF. The method disclosed in Kinstler is specific for the conjugation of G-CSF to PEG. It is not contemplated by Kinstler, nor those skilled in the art, that the method used to conjugate G-CSF to PEG can be used to conjugate other proteins or to use different synthetic particles and materials while retaining particular properties of the protein.

Thus, there is a need for a more universal method of conjugation and more particularly the use of better methods of conjugating proteins to monodisperse, well-defined synthetic particles.

SUMMARY OF THE INVENTION

In its broadest sense, the present invention is directed to orthogonal chemistry for site specific conjugation/ligation of synthetic particles to the N-terminus of proteins. Synthetic particles include monodisperse synthetic particles, highly monodisperse nanoscale particles, and dentritic polymers (herein after dendrimers). Proteins include four-helical bundle proteins and cytokines.

Dendrimers, a subset of highly monodisperse nanoscale particles (also known as dense star polymers), offer benefits that other carriers known in the art lack. In particular, dendrimers exhibit molecular architecture characterized by regular dendritic branching with radial symmetry. See U.S. Pat. No. 5,527,524 incorporated by reference. This uniform architecture is desirable for homogenous ligated compositions. In addition, each dendrimer can be molecularly tailored to meet specialized end uses by controlling the size, shape and properties of the dendrimer.

Cytokines are small proteins that engage cell-surface receptors to elicit their biological activities. Synthetic particles are any particulate materials produced using synthetic chemical means. Monodisperse synthetic particles are any particulate materials produced using synthetic chemical means that are limited to a single chemical composition, size and architecture. Monodisperse nanoscale particles are any particulate materials produced using synthetic chemical means that are limited to a single chemical composition, size and architecture and which measure between 1 and 999 nanometers in each dimension (ie., length, width and depth).

One method of conjugation contemplated by the present invention entails coupling of sulfhydryl-terminated synthetic particles with a maleimide spacer on the protein. Another contemplated method is based on using a serine end-terminal (amine end) on the protein that can then be oxidized using periodate to form an aldehyde. The aldehydic protein can then be coupled to the synthetic functionalized with an aminooxyacetyl group to form a stabilized oxime. A further method to achieve essentially the same result is to couple an amine-terminated synthetic particle to the aldehydic protein. The Schiff's base that is formed can then be stabilized using a mild reducing agent such as sodium cyanoborohydride.

DETAILED DESCRIPTION OF THE INVENTION

One type of specialized synthetic particles are dendrimers. Dendrimers are polymers that are unimolecular assemblages possessing: 1)an initiator core; 2) interior layers (referred to as generations or G) made up of repeating units, radially attached to the initiator core; and 3) exterior surface of terminal functionality or terminal functional groups attached to the outermost generation. The size and shape of the dendrimer and the resulting functionality can be controlled by the choice of the initiator core, the number of generations and the choice of the repeating units employed at each generation. Since dendrimers can be isolated at any particular generation, dendrimers can be obtained having only the desired structural properties. (See U.S. Pat. No. 5,527,524, incorporated by reference). Particular methods of producing dendrimers can be prepared according to methods described in U.S. Pat. No. 4,587,329, incorporated by reference.

PAMAM (polyamidoamine) dendrimers are microdomains which very closely mimic classical spherical micelles in shape, size, number of surface groups and area/surface groups. A significant difference between micelles and PAMAM dendrimers is that PAMAM dendrimers are covalently fixed and robust compared to the dynamic equilibrating nature of micelles. This difference provides an advantage for the PAMAM dendrimers especially when using them as encapsulation devices. This advantage is most appreciated when the PAMAM dendrimers remain in the fifth generation or less. Generations more than five may cause congestion at the surface.

Dendrimers suitable for this invention include those described in U.S. Pat. Nos. 4,507,466, 4,558,120, 4,568,737, 4,587,329, and 5,527,524, incorporated by reference.

Although all synthetic particles are contemplated by this invention, monodisperse synthetic particles are more preferred. A more preferred embodiment of the invention uses highly monodisperse nanoscale particles. An even more preferred embodiment uses PAMAM dendrimers.

Proteins for this invention are either joined directly to the synthetic particle or in an alternative embodiment attached via a linker. In order to prepare the protein for the linker type application a GMBS-linker may be employed. A commercially obtained (Pierce, Rockford, Ill., USA ) sulfo-GMBS (N-gamma-maleimidobutyryloxyl sulfosuccinimide ester) linker sequence was appended to the N-terminal alanine of the protein at a high pH to achieve N-terminal site specificity of GMBS linker attachment. For the non-linker/direct attachment method, proteins were engineered by standard biotechnology methods to contain a serine at the N-terminus.

Although all proteins can potentially be utilized for this invention, a more preferred embodiment uses four-helical bundle proteins. An even more preferred embodiment uses cytokines. The proteins used for this invention can be natural or recombinantly produced. A more preferred embodiment uses recombinant proteins engineered for particular purposes or bioactivity.

It is also contemplated that the synthetic particle or more specifically a dendrimer can be engineered to be ligated to more than one protein.

A preferred method for site specifically attaching a synthetic particle to the N-terminus of a protein comprises the steps of:

1) attaching a spacer on the N-terminus of a protein;
2) forming a sulfhydryl on a synthetic particle at the amine; and
3) combining said sulfhydrylized synthetic particle to said spacer on the protein.

A more preferred method for site specifically attaching a synthetic particle to the N-terminus of a protein comprises the steps of:

1) converting a ser-terminated protein to an aldehyde;
2) converting the amine of a synthetic particle to a oxiamine; and
3) combining said aldehyde ser-terminated protein to said synthetic particle at said oxiamine.

The following three schemes describe processes of preparing novel conjugates. It would be obvious from the schemes to those skilled in the art that alternate reagents and modifications of the processes could be used depending on circumstances. These schemes are not intended to limit the scope of the invention.

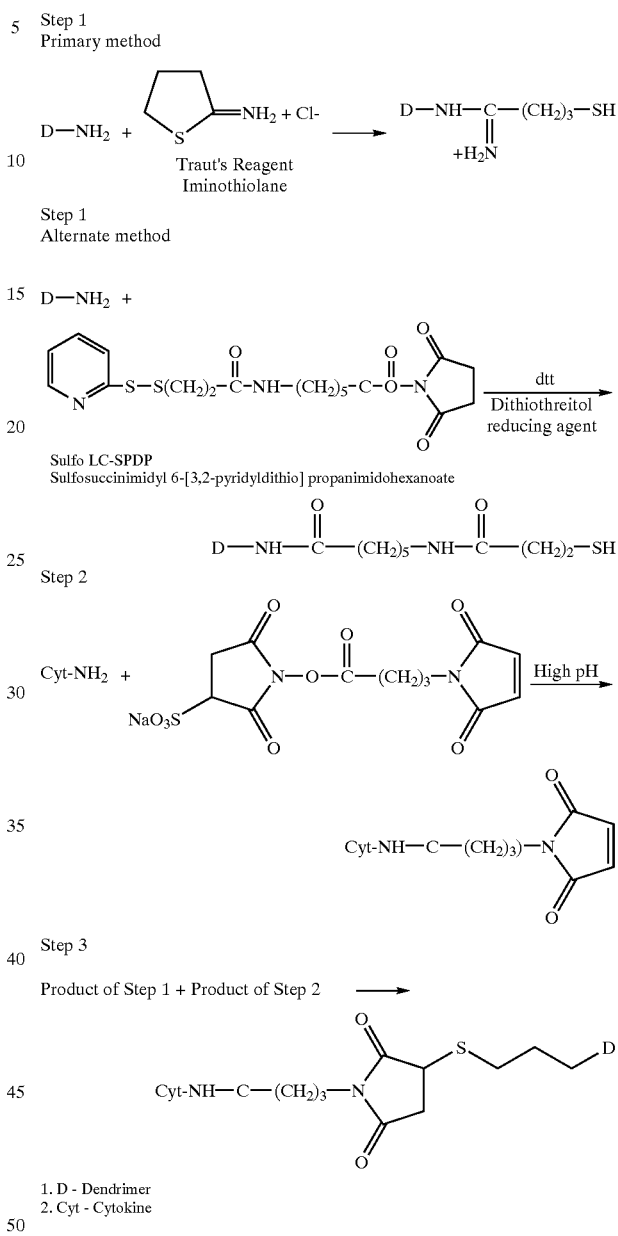

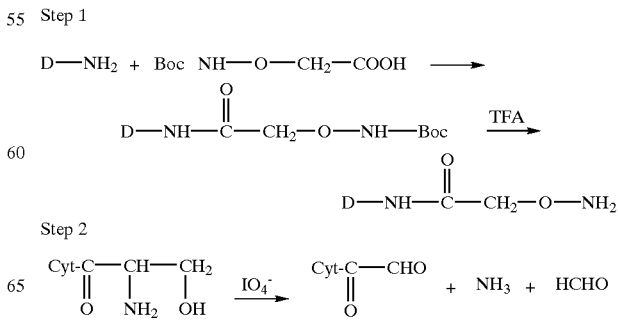

Step 3

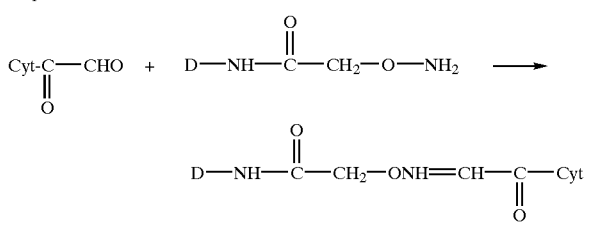

1. D - Dendrimer
2. Cyt - Cytokine
3. TFA - Trifluoroacetic acid

Scheme 3
Oxime Chemistry

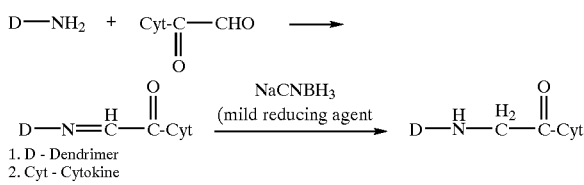

1. D - Dendrimer
2. Cyt - Cytokine

The following Examples are provided to illustrate the present invention and are not intended to !limit the scope thereof. Those skilled in the art will readily understand that known variations of the conditions and processes of the following preparative procedures can be used to prepare these conjugates.

Without further elaboration, it is believed that one skilled in the art can, using the preceding descriptions, utilize the present invention to its fullest extent. Therefore, the following preferred specific embodiments are to be construed as merely illustrative and not limitative of the remainder of the disclosure in any way whatsoever. Compounds containing multiple variations of the structural modifications illustrated in the preceding schemes or the following Examples are also contemplated.

The starting materials which are required for the above processes herein described are known in the literature or can be made by known methods from known starting materials.

EXAMPLE 1

Ex. 1a 0.1 mM of a cytokine (containing an N-terminal alanine residue) was reacted with sulfo-gmbs (γ-maleimido butyoloxy sulfosuccinimide) linker (0.2 mM) at pH 8.5 for 45 minutes, and then dialysed against phosphate buffered saline (PBS, pH 7.2, Life Technologies, Inc, Gaithersberg, Md.).

Ex. 1b

A 0.1 M solution of G-5 dendrimers were treated with nitrogen-purged 5 mM iminothiolane HCl, 1 mMEDTA in PBS to convert some of the dendrimer surface amines to sulfhydryls. After incubation for 45 minutes with constant nitrogen purging, the reaction mixture was dialysed against PBS.

Ex. 1c

After dialysis, GMBS-linker cytokine and sulfhydryl G-5 dendrimer were mixed (two parts GMBS-linker cytokine to one part G-5 dendrimer solution) and incubated for four hours at room temperature (rt).

EXAMPLE 2

Ex. 2a

A cytokine containing an N-terminal serine was reacted with a two-fold molar excess of sodium perodate for 15 minutes in 20 mM phosphate buffer (pH 7) to convert the epsilon amino group of the protein to an aldehyde. The solution was then dialysed against 50 mM NaOAc (pH 4.5).

Ex. 2b

Boc-aminooxyacetic acid was synthesized (Pochon et al., 1989) and mixed with G-5 dendrimer at 20-fold molar excess (relative to the number of dendrimer surface amines in the presence of EDC (same molar concentration as the Boc-aminooxyacetic acid) in PBS.

Ex. 2c

After reacting overnight, the reaction mixture was dialysed against water. Dendrimer solution was concentrated using a Centricon-20 (Amicon, Beverly, Mass.) and reacted with trifluoroacetic acid (TFA) for 60 minutes at room temperature.

Ex. 2d

Excess TFA was removed by exhaustive purging with nitrogen. Oxiamine dendrimers were resuspended and dialysed in water.

Ex. 2e

The oxiamine dendrimers were mixed with the aldehyde Ser-cytokine at a molar ratio of 1:1 and incubated overnight at room temperature. The conjugation reaction was then dialysed against 20 mM phosphates

STRUCTURAL ANALYSIS

Trypsin Digestion of Cytokine Derivatives
Modified for Dendrimer Conjugation

Dried sample was solubilized in 25 mM ammonium bicarbonate pH 7.8 for a final concentration of 1.2 mg/ml. Trypsin (Promega, Madison, Wis., USA) was added at a 1:60 (w/w) enzyme to substrate ratio and incubated for 6 hours at ambient temperature. Sample was mixed with matrix (33 mM alpha-cyano-4 hydroxycinnamic acid—Hewlett Packard, Palo Alto, Calif., USA) at a 1:8 (v/v) ratio. Approximately 8 pmole of digest was analysed by MALDI-TOF (Matrix assisted laser desorption ionization-time of flight).

Matrix Assisted Laser Desorption Ionization-Time
of Flight Analysis

MALDI analysis was performed on untreated cytokine of Ex. 1a, the product of Ex. 1a and the product of Ex. 2a using a PerSeptive Biosystem Voyager—DERP Benchtop MALDI-TOF Mass Spectrometer (Framingham, Mass., USA) with a 1.3 meter flight tube. Samples were run in the linear mode with delayed extraction using alpha-cyano-4 hydroxycinnamic acid matrix. Both trypsin digested (see above) and undigested samples were analyzed.

Untreated Cytokine of Ex. 1a and Untreated
Cytokine of Ex. 2a were Conjugated to Dendrimers
Site-specifically Attempts to identify a matrix suitable to volatilize dendrimer-untreated cytokine conjugates for MALDI TOF analysis were not successful (Data not shown). Therefore, MALDI-TOF analysis of the product of Ex. 1a and the product of Ex. 2a were used to demonstrate the site-specificity of protein modification (N-terminal GMBS linker addition or N-terminal oxidation to aldehyde group) for coupling, and therefore of dendrimer-protein conjugation.

Analysis of untreated cytokine of Ex. 1a (FIG. 1) reveals a single predominant peak at the predicted average mass, with minor peak occurring at about at 20 AMU higher molecular weight. Addition of the product of Ex. 1a to untreated cytokine of Ex. 1a increases its mass by 169 AMU (FIG. 2): this species is detected in the chromatograph (FIG. 2), though substantial amounts of the starting materials remain. In the case of untreated cytokine of Ex. 2a oxidized to have an N-terminal aldehyde, cytokine molecular weight is reduced by about 31 AMU (FIG. 3), as was predicted. A minor band of unoxidized cytokine of Ex. 2a is also detected. These data indicate that significant fractions of the parent proteins were converted to conjugation-ready form and that the conjugation-ready forms of the proteins contain primarily a single modification per protein molecule.

Figure 2:
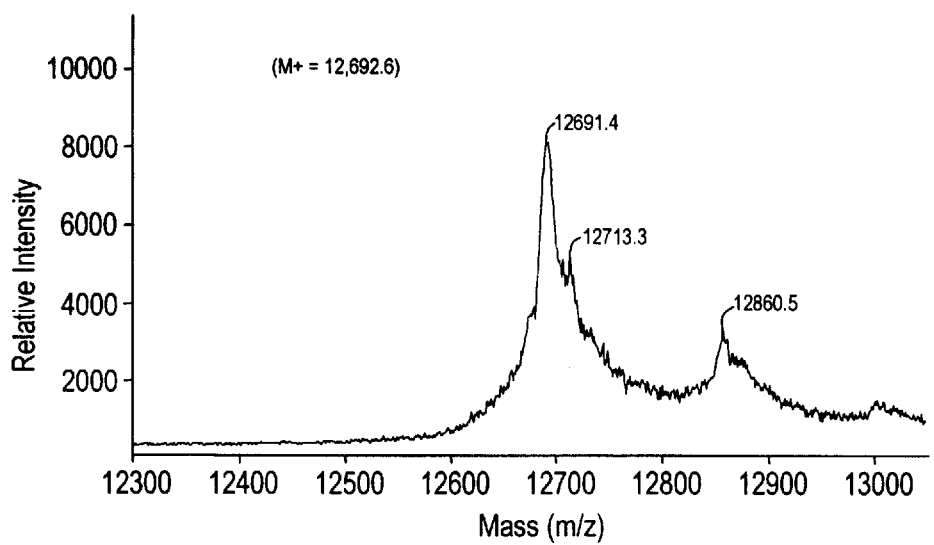
Figure 3:
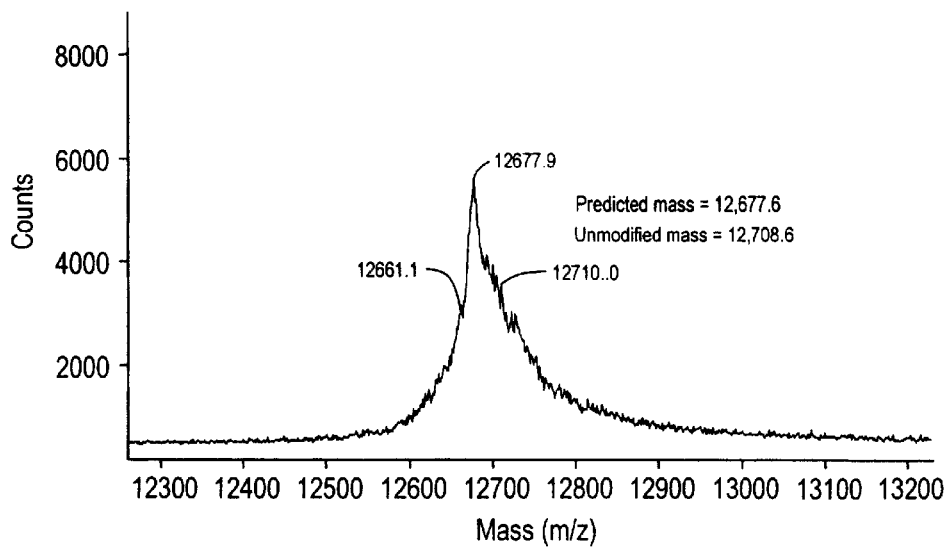

FIGS. 1, 2 and 3. MALDI analysis of untreated cytokine of Ex. 1a species activated for dendrimer conjugation.

FIG. 1: Unactivated untreated cytokine of Ex. 1a.

FIG. 1: Product of Ex 1a. (Activated for maleimide/sulfhydryl conjugation); and

FIG. 1: Product of 2a. (activated for oxiamine conjugation)

Figure 4:
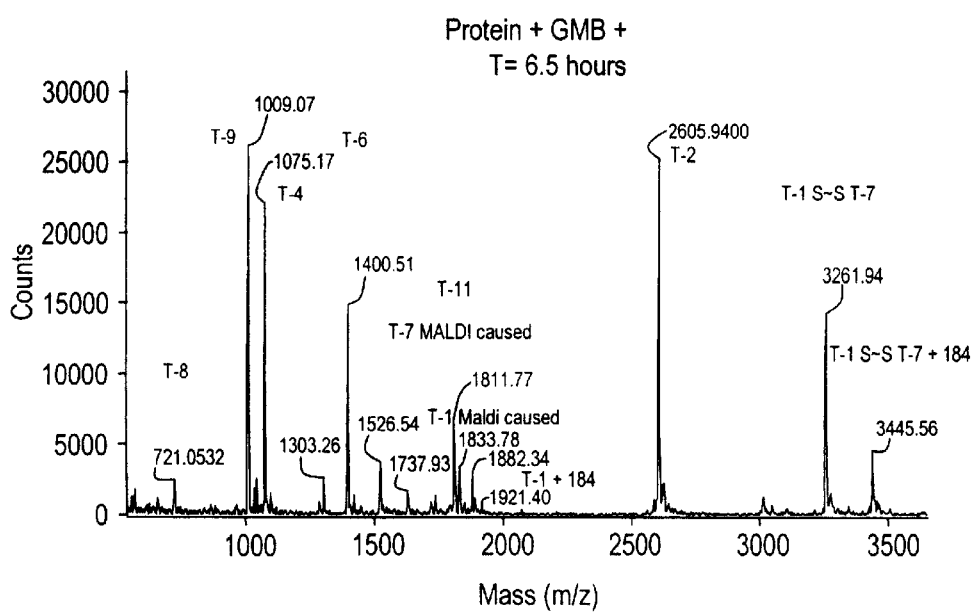
Figure 5:
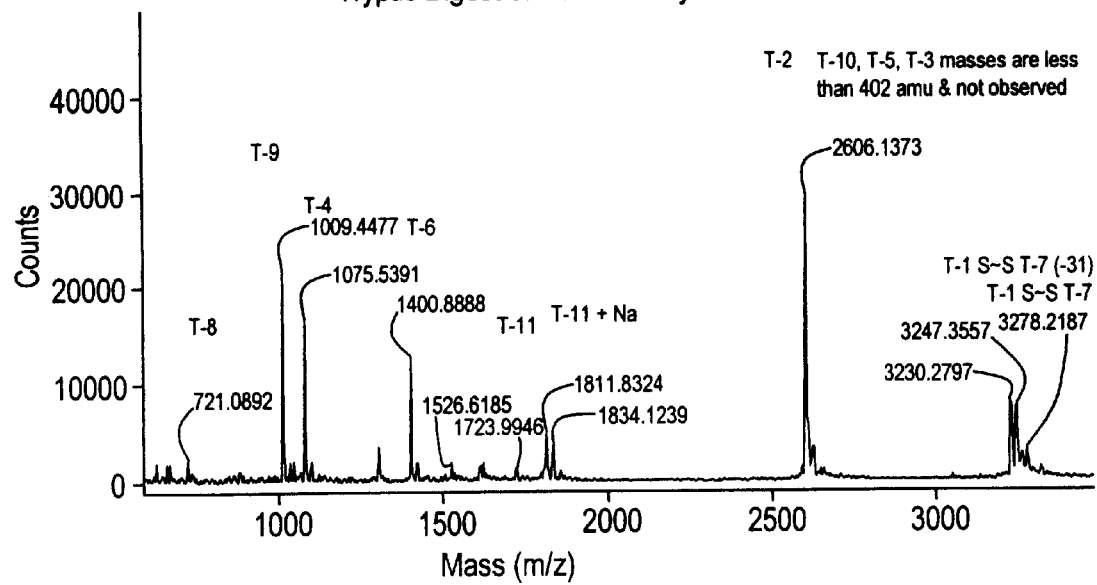

Analysis of tryptic digest fragments of untreated cytokine of Ex. 1a modified for conjugations was used to localize the position of modification for conjugation. Sites of trypsin cleavage are shown in FIG. 4 and predicted masses of digest fragments are presented in FIG. 5. MALDI-TOF chromatographs of tryptic digests of the product of Ex 1a and the product of Ex. 2a are shown in FIG. 4 and FIG. 5 respectively. With the exception of low molecular weight fragments (T-3, T-5 and T-10), predicted tryptic digestion fragments can be accounted for both chromatographs. Note that because the experiment was not performed under reducing conditions, fragments T-1 and T-7 appear together as disulfide-linked peptides.

In the case of the product of Ex 1a, addition of the linker is expected to increase the mass of the T-1-T-7 linked peptides by 169: this fragment is not detected in the chromatograph, though a fragment corresponding to the T-1-1-7 peptide plus 184–185 AMU is (FIG. 4). Presumably, this is due to an adduct that was formed during the tryptic digest. Nonetheless, sufficient additional mass to account for the GMBS linker appended to untreated cytokine of Ex. 1a (FIG. 4) is not associated with other tryptic fragments, so the results are consistent with the interpretation that a single GMBS linker is linked to the N end of untreated cytokine of Ex. 1a.

The mass of T-1-T-7 fragment of product of Ex. 2a should be 3,246.8 (FIG. 5), and such a fragment is present in the chromatograph. Unoxidized T-1-T-7 can also be detected.

Thus, oxidation of untreated cytokine of Ex. 2a and GMBS linker addition to untreated cytokine of Ex. 1a can be detected by MALDI-TOF. In both cases, the cytokines are predominantly modified once per molecule, and the modifications are localized to the T-1-T-7 trypsin digestion fragments. These data support the notion that conjugation to dendrimers occured at the N-terminus of the cytokine molecules, as desired.

FIGS. 4 and 5. Maldi-TOF analysis of trypsin digests of cytokine activated for coupling to dendrimers.

FIG. 4: The product of Ex. 1a (For sulfhydryl/maleimide conjugation) and

FIG. 5: The product of Ex. 2a (For oxiamine conjugation.

| Fragment | MW (daltons) |
|---|---|
| T-1 (untreated cytokine of Ex. 1a) | 1738.09 |
| T-1 (product of Ex. 2a) | 1723.09 |
| T-1 (untreated cytokine of Ex. 2a) | 1754.09 |
| T-2 | 2605.94 |
| T-3 | 402.47 |
| T-4 | 1075.26 |
| T-5 | 317.41 |
| T-6 | 1400.58 |
| T-7 | 1526.76 |
| T-8 | 720.94 |
| T-9 | 1009.07 |
| T-10 | 276.31 |
| T-11 | 1812.03 |

Predicted masses of tryptic fragments of untreated cytokine of Ex. 1a, untreated cytokine of Ex. 2a and their derivatives used in dendrimer conjugation. Note that the T-1 and T-7 fragments are disulfide linked. In the end product of Ex 2a the predicted combined mass of T-1 and T-7 is 3,246.8.

FUNCTIONAL ANALYSIS

Quantitative Amino Acid Analysis of Proteins and Conjugates

Quantitative amino acid analysis (Moore and Stein, 1963) was used to quantify the protein concentration of untreated cytokine-dendrimer conjugate solutions. Protein-dendrimer conjugates were subjected to vapor phase acid hydrolysis using 6N HCl (with 1% phenol added) for 1.5hours at 150° C. (Bidlingmeyer et al. 1984). A Water's Pico-Tag workstation (Waters, Midford, Mass., USA) was used for the hydrolysis. The resulting hydrolysate was analyzed by post-column ninhydrin amino acid analysis on a Beckman model 6300 amino acid analyzer (Beckman, Inc, Palo Alto, Calif., USA).

hIL-3 Receptor Binding Assay

Baby hamster kidney (BHK) cells which had been stably transfected with the gene for the IL-3 receptor subunit (BHK") isolated from AML 193.1.3 cells were used in receptor binding studies (Thomas et al., 1995). The transfected BHK" cells were grown in Dulbecco's Modified Eagle Media, 5% FBS, 2 mM glutamine and harvested using Cell Dissociation Media (Sigma Chemical Company; St. Louis, Mo.). The BHK" cells were washed and then resuspended in assay media (Iscove's Modified Dulbecco's Media, 5% FBS, 0.2% sodium azide) and kept frozen at −20° C. until their use in the binding assays. Assay incubations (0.1 ml), containing the radioligand (radio labeled hIL-3 receptor agonist; 300–500 pM) and competing compound were performed at 0–4° C. and initiated by the addition of ice cold cells. Incubations were halted by separation of bound and free radiolabel by rapid centrifugation (12000×g for one min) in an Eppendorf 5415C centrifuge. The supernatant was aspirated and the tube tip containing the cell pellet with the associated radioactivity cut off and counted in an ICN Micromedics System automatic gamma counter. Nonspecific binding was defined as the residual binding occurring in the presence of excess standard hIL-3 receptor agonist (1000 nM). Radio labeled hIL-3 receptor agonist competition binding experiments were analyzed using Scatchard and Hill transformations and the $IC_{50}$ values for compounds determined using logit-log analysis. The radio labeled hIL-3 receptor agonist [$^{125}$I], a fully bioactive hIL-3 receptor agonist with a 14 amino acid N-terminal extension to facilitate radioiodination (Thomas et al. 1995), was used in these experiments was iodinated by the lactoperoxidase method and had specific activities of 500–2000 Ci/mmol as measured by ELISA or self displacement analysis.

Untreated Cytokine of Ex. 1a Conjugated to Dendrimers Recognize the hIL-3 Receptor Receptor binding experiments revealed that both dendrimer-cytokine conjugates retained the ability to recognize the hIl-3 receptor alpha subunit. The affinity of untreated cytokine of Ex. 2a and the product of Ex. 1a were comparable, and their receptor binding was two to fourfold less avid than unmodified untreated cytokine of Ex. 1a (W. Hood, unpublished, B. Klein et al, manuscript in preparation). Both conjugates exhibited modest decreases in receptor affinity relative to the corresponding precursor molecule, with conjugate binding about fourfold less avid than free protein.

| Sample | $IC_{50}$ (nM) |
|---|---|
| Product of Ex. 1a | 5.4 ± 1.2 |
| Sulfhydryl/maleimide conjugate | 24.0 ± 1.6 |

-continued

| Sample | $IC_{50}$ (nM) |
|---|---|
| Untreated cytokine of Ex. 2a | 4.45 ± 0.8 |
| Oxime conjugate | 17.0 ± 1.5 |

Affinities of cytokine species and their dendrimer conjugates for the hIL alpha receptor subunit. $IC_{50}$ values were calculated in nM untreated cytokine of Ex. 1a of the conjugate as determined by amino acid composition analysis. The presented affinities are the mean of three independent determinations, and standard error values (SE) are shown.

We claim:

1. A method for site specifically attaching a synthetic particle to the N-terminus of a protein, said method comprising the steps of:

a) converting a polypeptide containing a serine as its N-terminal amino acid to an aldehyde;

b) converting the amine of a synthetic particle to a oxiamine; and c) combining said aldehyde polypeptide containing a serine as its N-terminal amino acid to said synthetic particle at said oxiamine.

* * * * *